US005686306A

United States Patent [19]

West et al.

[11] Patent Number: 5,686,306
[45] Date of Patent: *Nov. 11, 1997

[54] METHODS AND REAGENTS FOR LENGTHENING TELOMERES

[75] Inventors: Michael D. West, San Carlos, Calif.; Jerry Shay, Dallas; Woodring E. Wright, Arlington, both of Tex.

[73] Assignee: Board of Regents, The University of Texas System, Austin, Tex.

[*] Notice: The portion of the term of this patent subsequent to Jun. 7, 2015, has been disclaimed.

[21] Appl. No.: 337,684

[22] Filed: Nov. 10, 1994

Related U.S. Application Data

[63] Continuation-in-part of Ser. No. 151,477, Nov. 12, 1993, and Ser. No. 153,051, Nov. 12, 1993, Pat. No. 5,618,668, each is a continuation-in-part of Ser. No.60,952, May 13, 1993, which is a continuation-in-part of Ser. No. 38,766, Mar. 24, 1993, Pat. No. 5,489,508, which is a continuation-in-part of Ser. No. 882,438, May 13, 1992, abandoned.

[51] Int. Cl.$^6$ ............................... C12N 5/10; C12N 5/12; C07H 21/00; C07H 21/07
[52] U.S. Cl. .................... 435/346; 435/6; 435/375; 536/23.1
[58] Field of Search ................. 435/6, 70.2, 172.2, 435/91.1, 240.1, 240.2, 240.26, 325, 346, 375, 377, 384, 405; 514/44; 536/23.1, 24.1, 24.3, 24.33, 24.5

[56] References Cited

U.S. PATENT DOCUMENTS

| 4,737,454 | 4/1988 | Dattagupta et al. | 536/24.31 |
| 5,489,508 | 2/1996 | West et al. | 435/6 |

FOREIGN PATENT DOCUMENTS

| 9304546 | 5/1993 | WIPO . |
| 9408053 | 4/1994 | WIPO . |

OTHER PUBLICATIONS

Gura, "Antisense has growing pains" Science 270:575–577, Oct. 1995.
Johnston et al. "Present status and future prospects for HIV therapies" Science 260:1286–1293, May 1993.
Milligan et al. "Current concepts in antisense drug design" J. Medicinal Chem. 36(14):1924–1937, Jul. 1993.
Tseng et al. "Antisense oligonucleotide technology in the development of cancer therapeutics" Cancer Gene Therapy 1(1):65–71, Mar. 1994.
Cotten, "The in vivo application of ribozymes." Trends in Biotechnology 8:174–178 (1990).
Counter et al., "Stabilization of Short Telomeres and Telomerase Activity Accompany Immortalization of Epstein–Barr Virus–Transformed Human B Lymphocytes." J. Virology 68:3410–3414 (1994).
Counter et al., "Telomerase activity in human ovarian carcinoma." Proc. Natl. Acad. Sci. USA 91:2900–2904 (1994).

Greider and Blackburn, "A telomeric sequence in the RNA of Tetrahymena telomerase required for telomere repeat synthesis," Nature 337:331–337 (1989).
Harley et al., "The Telomere Hypothesis of Cellular Aging," Experimental Gerontology 27:375–382 (1992).
Shay et al., "Loss of telomeric DNA during aging may predipose cells to cancer (Review)," Int'l J. Oncology 3:559–563 (1993).
Strahl and Blackburn, "The effects of nucleoside analogs on telomerase and telomeres in Tetrahymena," Nucleic Acids Research 22:893–900 (1994).
Windle and McGuire, "Telomeres: the long and the short of it," Proceedings of the American Association for Cancer Research 33:594–595 (1992).
Allsopp et al., "Telomere Length Predicts Replicative Capacity of Human Fibroblasts," Proc. Natl. Acad. Sci. USA 89:10114–10118 (1992).
Klingelhutz et al., "Restoration of Telomeres in Human Papoillomavirus–Immortalized Human Anogential Epithelial Cells," Molecular and Cellular Biology 14:961–969 (1994).
Grieder and Blackburn, "The Telomere Terminal Transferase of Tetrahymena Is a Ribonucleoprotein Enzyme with Two kinds of Primer Specificity", 51 Cell 887, 1987.
Blackburn et al., "Recognition and elongation of telomeres by telomerase", 31 Genome 553, 1989.
Greider, "Telomerase Is Processive", 11 Molec. and Cell. Biology 4572, 1991.
Counter et al., "Telomere shortening associated with chromosome instability is arrested in immortal cells which express telomerase activity", 11 EMBO 1921, 1992.
Harley, "Telomere loss: mitotic clock or genetic time bomb?", 256 Mutation Res. 271, 1991.
Eck and Nabel, "Antisense oligonucleotides for therapeutic intervention", 2, Opin. Biotech 897, 1991.
Zahler et al., "Inhibition of telomerase by G–quartet DNA structures", 350 Nature, 718, 1991.
Yu and Blackburn, "Developmentally Programmed Healing of Chromosomes by Telomerase in Tetrahymena", 67 Cell 823, 1991.
Harley et al., "Telomeres shorten during ageing of human fibroblasts", 345 Nature 458, 1990.
Blackburn, "Structure and function of telomeres", 350 Nature 569, 1991.
Cech, "Ribozymes and Their Medical Implications", 260 JAMA 3030, 1988.
S. Wang and V. Zakian (1990) Nature 345:456. Telomere–telomere recombination provides an express pathway for telomere acquisition.

(List continued on next page.)

Primary Examiner—John L. LeGuyader
Assistant Examiner—Thomas G. Larson
Attorney, Agent, or Firm—Kevin Kaster; Richard J. Warburg; Amy S. Hellenkamp

[57] ABSTRACT

Method and compositions for increasing telomere length in normal cells can be used to increase the proliferative capacity of cells and to delay the onset of cellular senescence.

3 Claims, 3 Drawing Sheets

OTHER PUBLICATIONS

S. Goldstein (1990) Science 249:1129. Replicative senescence: the human fibroblast comes of age.

J. Smith and R. Whitriey (1980) Science 207:82. Intracional variation in proliferative potential of human diploid fibroblasts:stochastic mechanisms for cellular aging.

T. Ohno (1979) Mechanisms of aging and development 11:179. Strict relationship between dialyzed serum concentration and cellular life span in vitro.

L. Hayflick and P. Moorhead (1961) Experimental Cell Research 25:585. The serial cultivation of human diploid cell strains.

J. Szostak (1989) Nature 337:303. The beginning of the ends.

G. Jankovic, et al. (1991) Nature 350:197. Telomere loss and cancer.

J. Gall (1990) Nature 344:108. Typing up loose ends.

G. Yu, et al. (1990) Nature 344:126. In vivo alteration of telomere sequences and senescence caused by mutated Tetrahymena telomerase RNAs.

L. Harrington and C. Greider (1991) Nature 353:451. Telomerase primer specificity and chromosome healing.

J. Gray, et al. (1991) Cell 67:807. Cloning and expression of genes for the Oxytricha telomere–binding protein:specific subunit interactions in the telomeric complex.

F. Muller, et al. (1991) Cell 67:815. New telomere formation after developmentally regulated chromosomal breakage during the process of chromosome diminution in *Ascarls lumbricoides*.

C. Greider (1990) Bloessays 12:363. Telomers, telomerase and senesence.

E. Henderson, et al. (1990) Biochemistry 29:732. Telomere G–strand structure and function analyzed by chemical protection, base analogue substitution, and utilization by telomerase in vitro.

D. Gottschling, et al. (1990) Cell 63:751. Position effect at *S. cerevisiae* telomeres: reversible repression of Pol II transcription.

V. Lundblad and J. Szostak (1989) Cell 57:633. A mutant with a defect in telomere elongation leads to senescence in yeast.

E. Blackburn (1984) Annual Reviews in Biochemistry 53:163. The molecular structure of centromeres and telomeres.

A. Olovnikov (1973) J. Theoretical Biology 41:181. A theory of marginotomy.

H. Cooke and B. Smith (1986) CSHSQB LI:213. Variability at the telomeres of the human X/Y pseudoautosomal region.

C. Greider (1991) Cell 67:645. Chromosome first aid.

G. Morin (1989) Cell 59:521. The human telomere terminal transferase enzyme is a ribonucleoprotein that synthesizes TTAGGG repeats.

C. Harley, et al. (1990) Nature 345:458. Telomeres shorten during ageing of human fibroblasts.

Ham and McKeehan (1979) Methods in Enzymology LVIII:44. Media and growth requirements.

J. Starling, et al. (1990) Nucleic Acids Research 18:6881. Extensive telomere repeat arrays in mouse are hypervariable.

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) SEQUENCE DESCRIPTION: SEQ ID NO: 1:

TTAGGGTTAG GG                                                                                    12

( 2 ) INFORMATION FOR SEQ ID NO: 2:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear     ( i i ) SEQUENCE DESCRIPTION: SEQ ID NO: 2:

TTAGGG                                                                                            6

( 2 ) INFORMATION FOR SEQ ID NO: 3:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear     ( i i ) SEQUENCE DESCRIPTION: SEQ ID NO: 3:

TTAGGGTTA                                                                                         9

( 2 ) INFORMATION FOR SEQ ID NO: 4:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( i i ) SEQUENCE DESCRIPTION: SEQ ID NO: 4:

TCGAGCACAG TT                                                                                     12

( 2 ) INFORMATION FOR SEQ ID NO: 5:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( i x ) FEATURE:
        ( D ) OTHER INFORMATION: The letter "W" stands for T
            or A.

( i i ) SEQUENCE DESCRIPTION: SEQ ID NO: 5:

GWGWGWGWGW GW                                                                                     12

( 2 ) INFORMATION FOR SEQ ID NO: 6:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( i i ) SEQUENCE DESCRIPTION: SEQ ID NO: 6:

CCCTAACCCT AA                                                                                     12

( 2 ) INFORMATION FOR SEQ ID NO: 7:

( i ) SEQUENCE CHARACTERISTICS:
        ( A ) LENGTH: 18 base pairs
        ( B ) TYPE: nucleic acid (C) STRANDEDNESS: single
(D) TOPOLOGY: linear (i i) SEQUENCE DESCRIPTION: SEQ ID NO: 7:

TTAGGGTTAG GGTTAGGG   18

(2) INFORMATION FOR SEQ ID NO: 8:

(i) SEQUENCE CHARACTERISTICS:
(A) LENGTH: 10 base pairs
(B) TYPE: nucleic acid
(C) STRANDEDNESS: single
(D) TOPOLOGY: linear (i i) SEQUENCE DESCRIPTION: SEQ ID NO: 8:

TTAGGTTAGG   10

METHODS AND REAGENTS FOR LENGTHENING TELOMERES

CROSS-REFERENCE TO RELATED APPLICATIONS

The present application is a continuation-in-part of U.S. patent application Ser. Nos. 08/151,477, and 08/153,051, now U.S. Pat. No. 5,618,668, both of which were filed Nov. 12, 1993, which are continuations-in-part of Ser. No. 08/060,952, filed May 13, 1993, which is a continuation-in-part of Ser. No. 08/038,766, filed Mar. 24, 1993, Mar. 10, 1997, now U.S. Pat. No. 5,489,508, which is a continuation-in-part of now abandoned Ser. No. 07/882,438, filed May 13, 1992. Each of the foregoing patent applications is incorporated herein by reference.

BACKGROUND OF THE INVENTION

1. Field of the Invention

This invention relates to methods and reagents for extending the telomeres and therefore the proliferative capacity of cells. The invention therefore relates to the fields of chemistry, pharmacology, biology, molecular biology, and medical therapeutic and diagnostic technology.

2. Description of Related Art

Normal human somatic cells (i.e., fibroblasts, endothelial, and epithelial cells) display a finite replicative capacity of 50–100 population doublings characterized by a cessation of proliferation in spite of the presence of growth factors. This cessation of replication in vitro is variously referred to as cellular senescence or cellular aging. See, Goldstein, 1990, *Science* 249:1129, and Hayflick and Moorehead, 1961, *Exp. Cell Res.* 25:585. The replicative life span of cells is inversely proportional to the in vivo age of the donor, so cellular senescence is believed to play an important role in aging in vivo. See Martin et. al., 1979, *Lab. Invest.* 23:86, and Schneider and Mitsui, 1976, *Proc. Natl. Acad. Sci. U.S.A.* 73:3584.

Cellular immortalization (the acquisition of unlimited replicative capacity) may be thought of as an abnormal escape from cellular senescence. See Shay et al., 1991, *Exp. Cell Res.* 196:33. Normal human somatic cells appear to be mortal and to have finite replicative potential. In contrast, germline and malignant tumor cells appear to be immortal and to have indefinite proliferative potential. Human cells cultured in vitro appear to require the aid of transforming viral oncoproteins to become immortal, and even then, the frequency of immortalization is $10^{-6}$ to $10^{-7}$. See Shay and Wright, 1989, *Exp. Cell Res.* 184:109. Cells obtained from murine sources immortalize at a relatively high frequency without the aid of transforming oncoproteins. A variety of hypotheses have been advanced over the years to explain the causes of cellular senescence.

Shay et al., 1992, *Experimental Gerontology* 27:477, and Shay et al., 1991, *Exp. Cell Res.* 196:33, describe a two-stage model for human cell mortality to explain the ability of Simian Virus 40 (SV40) T-antigen to immortalize human cells. The mortality stage 1 mechanism (M1) is a mechanism by which cells cease to proliferate after a certain number of population doublings, and the biological molecules that carry out this mechanism appear to be the target of certain tumor virus proteins. An independent mortality stage 2 mechanism (M2) produces crisis in cells that have bypassed M1, with crisis being typified by severe chromosomal abnormalities and ultimately cell death. The M2 mechanism thus prevents tumor viruses from directly immortalizing human cells. The papers noted above describe experiments in which T-antigen expression was driven by a mouse mammary tumor virus promoter to cause reversible immortalization of cells. SV40 T-antigen extends the replicative life span of human fibroblasts by an additional 40–60%. The M1 mechanism is overcome by T-antigen, perhaps by binding to various cellular proteins or by inducing new activities to repress the M1 mortality mechanism. The M2 mechanism then causes cessation of proliferation, even though the M1 mechanism is blocked. Immortality is achieved only when the M2 mortality mechanism is also disrupted. The M2 mechanism appears to cause a dominant repression of the immortal phenotype, because hybrids between mortal and immortal human cells are generally mortal. See Pereira-Smith and Smith, 1983, *Science* 221: 964–966. As described above, such hybrids between murine cells immortalize at a much higher frequency, so it is relatively easy to obtain immortal hybrids between murine lymphocyte and myeloma cells to obtain immortal antibody-producing hybridomas, for instance. However, such hybrids are not immortal when produced with human cells.

The finite replicative capacity of cells may reflect the work of a "clock" linked to DNA synthesis at the telomeres (ends) of chromosomes. Thus, Harley et al., 1990, *Nature* 345:458, state that the amount and length of telomeric DNA in human fibroblasts decreases as a function of serial passage during aging in vitro. Harley, 1991, *Mutation Research* 256:271, describes that telomeres of human somatic cells act as a mitotic clock, shortening with age both in vitro and in vivo in a replication dependent manner and proposes a hypothesis for human cell aging and transformation in which telomeres and telomerase, a ribonucleoprotein polymerase involved in telomeric DNA synthesis, play a causal role in cell senescence and cancer.

PCT patent publication No. 93/23572 describes therapeutic and diagnostic methods relating to telomerase and telomere length. The publication describes oligonucleotide reagents that either reduce loss of telomere length during passage of cells in vitro or increase telomere length of immortal cells in vitro.

There remains a need for reagents that can increase telomere length in mortal cells and methods for extending the proliferative capacity of mortal cells and hybrids between mortal and immortal human cells. The present invention meets these and other needs, as described below, first in summary fashion and then in detail with examples.

SUMMARY OF THE INVENTION

The present invention provides a method for increasing the proliferative capacity of normal cells, which method comprises culturing or cultivating said cells in the presence of a therapeutically effective amount of an oligonucleotide substrate for telomerase under conditions such that said oligonucleotide substrate enters said cells and acts to lengthen telomeric DNA of said cells. The therapeutic method of this invention postpones cellular senescence in cells, and is especially useful for cells expressing telomerase and for hybrids between immortal and mortal cells. The method can also be used to reduce the level of chromosomal fusions and other chromosomal aberrations by increasing the telomere repeat length in cells.

While the cells treated by the present method can be cultured or cultivated in vivo during administration of the oligonucleotide, the invention has particular application to the cultivation of cells ex vivo, and provides especially important benefits to therapeutic methods in which cells are cultured ex vivo and then reintroduced to a host. Especially preferred examples of such cells include the CD4+ cells and the CD8+ cells of HIV-infected individuals and immune cells of aged people. The method is also preferred for increasing the replicative capacity of hybrids between immortal and mortal human cells, such as hybrids between human B-lymphocytes and myeloma cells, to increase the replicative capacity of antibody producing human hybridomas.

While the method of the invention is applicable to any normal cell type, the method can be practiced using normal cells that express a low level of telomerase activity. For purposes of the present invention, the term "normal" refers to cells other than tumor cells, cancer calls, or transformed cells. Especially preferred cells for use in the present method include embryonic, fetal, neonatal, and adult stem cells of any organ, and adult pluripotent hematopoietic stem cells. The method can also be applied to immortalized or transformed cells, such as myeloma cells, to increase telomere length prior to hybridization with a mortal cell.

The reagents of the invention include any oligonucleotide substrate for telomerase. The oligonucleotides of the invention can be composed of naturally occurring nucleotides or synthetic nucleotides or synthetic nucleotide analogs or combinations of any of the same. Typically, such oligonucleotides will be at least 12 nucleotides in length or longer.

These and other aspects of the invention are described in more detail below, beginning with a brief description of the accompanying drawings.

DESCRIPTION OF THE PREFERRED EMBODIMENTS

All normal diploid vertebrate cells have a limited capacity to proliferate, a phenomenon that has come to be known as the Hayflick limit or replicative senescence. In human fibroblasts, this limit occurs after 50–100 population doublings, after which the cells remain in a viable but non-dividing senescent state for many months. This contrasts to the behavior of most cancer cells, which have escaped from the controls limiting their proliferative capacity and are effectively immortal.

One hypothesis to explain the cause of cellular senescence concerns the role of the distal ends of chromosomes called telomeres. DNA polymerase synthesizes DNA in a 5'-to-3' direction and requires a primer to initiate synthesis. Because of the mechanism of action of DNA polymerase, the "lagging strand" is not replicated to the very end of a linear chromosome, as there is no means to initiate synthesis at the end of this strand. The chromosome is thus shortened with every cell division.

Telomeres comprise long stretches of duplex nucleic acid composed of a repeating sequence, called the "telomeric repeat," which in humans is 5'-TTAGGG-3' (SEQ. ID. NO:2). In addition, the G-rich strand of the telomere is longer than the C-rich strand; consequently, telomeres also comprise a single-stranded region composed entirely of telomeric G-rich repeat sequences. The enzyme telomerase is believed to mediate the synthesis of at least the terminal portion of the G-rich strand of the telomere. The cellular senescence hypothesis is that somatic cells lack telomerase and so lack the ability to replicate the very ends of DNA molecules. This results in a progressive shortening of the ends of the chromosomes with each cell division until a point at which this progressive loss signals functional changes, at which time the cell loses the capacity to proliferate.

When a cell loses in this manner the capacity to proliferate, the cell is senescent. Thus, the term "senescence" refers to the loss of ability of a cell to replicate in the presence of normally appropriate mitogenic signals. Senescence is also typically accompanied by a change in expression patterns of one or more genes. For instance, senescence in some cells is accompanied by an increase in the expression of degradative enzymes, such as collagenase. The term senescence does not include quiescent cells that can be induced to re-enter the cell cycle under appropriate conditions.

Thus, the length of a telomere is directly correlated to the life span of an individual cell. Certain populations of cells may lose telomere length at a greater rate than other cells within an individual, and those cells with shortened telomeres may thus become age-limiting within an individual organism. In such cases, important benefits can be achieved by slowing the loss of telomere sequences, which can be achieved by increasing the length of telomeric DNA.

The present invention provides a method for increasing the length of telomeres in normal cells and in hybrids between normal and immortal cells, thus extending the ability of a cell or hybrid to replicate and increasing the proliferative capacity of the treated cell. In this method, a telomere-extending amount of an agent that increases telomere length within the cell is provided to the cell. Specifically, the telomeres within a particular cell population can be lengthened by provision of an oligonucleotide that acts to lengthen telomeres in cell culture or cultivation, thus increasing the number of cell divisions that can occur before a cell becomes senescent. By virtue of the present method, one can lengthen telomeres by providing a nucleic acid, e.g., DNA or RNA (including modified forms), that can act as a telomerase substrate to the cells. Such nucleic acids typically include at least 2 to 3 telomeric repeat sequences, which in humans is 5'-TTAGGG-3' (SEQ. ID. NO:2).

This method is useful for the treatment of individuals not suffering from any particular condition but in which one or more cell types are limiting in that individual. The method thus can be practiced to delay the onset of cell senescence, which, as noted above, is characterized by the inability of that cell to replicate further in an individual. When practiced in this way, the method is a disease prevention method. The present invention also provides important new methods for treating disease, especially diseases characterized by an increased rate of proliferation of one or more particular groups of cells. An increase in the rate of proliferation increases the rate at which telomeric DNA is lost and the rate at which cells become senescent. The present method can be used to prevent the detrimental effects of early senescence of the cells due to increased cellular turnover associated with the disease.

The present invention also has application in tissue culture techniques to delay the onset of cellular senescence, whether for therapeutic or other purposes, such as manufacturing and research purposes. For instance, many cell-based therapies require the clonal expansion of cells for later reintroduction into a patient. During the expansion process, however, the cells continue to approach the Hayflick limit, so the cells reintroduced to the patient may be senesecent or close (i.e., within a few divisions) to a senescent state. This invention allows the expansion of cells in the presence of telomere lengthening agents and so provides a means to avoid the problems associated with cell senescence.

In addition, the present invention allows normal cells to be cultivated for extended doublings in vitro.

Although the present invention has a wide variety of applications, the invention has application in an area of critical importance today: cell therapy. Cell therapy involves the isolation of healthy human cells, the expansion of those cells ex vivo, and the reinfusion of the expanded cells into a patient. Cell therapy has application in the treatment of cancer and organ transplantation and many other disease states or conditions. For instance, bone marrow therapy takes advantage of the fact that bone marrow, the major organ of the immune system, is responsible for production of various cells in the blood from hematopoietic stem cells. Physicians treat hematological disorders such as anemia, leukemia, and lymphoma through bone marrow transplantation, in which bone marrow is removed from a donor (allogenic transplant) or a patient (autologous transplant) through general surgery, frozen and stored, and then transfused into the patient at a later date. Once transfused into the patient, the bone marrow cells gravitate to the bone marrow and engraft, eventually producing new blood cells either to increase the number of such cells in the anemic patient or to reconstitute the bone marrow destroyed as a result of chemotherapy or radiation therapy. Such methods suffer from the fact that autologous transplants often reintroduced diseased cells into the patient and allogenic transplants caused graft versus host disease.

To avoid such problems, methods have been developed to identify closely-matched donors (with respect to blood type and HLA markers) and to isolate the self-renewing hematopoietic stem cells, which generate all red blood cells, neutrophils, T and B lymphocytes, platelets, and macrophages, as well as other differentiating cells, from other, including diseased, cells. A variety of such separation methods have been developed (see, e.g., PCT patent publication 94/16715), especially for CD34+ cells, a small subset of which are believed to be the ultimate progenitor cell of the hematopoietic system. Due to the problems associated with bone marrow removal surgery and to the advances made in stem cell isolation, however, clinicians developed methods for isolating stem cells from peripheral blood, expanding those cells in culture, and then reintroducing the expanded cells into the patient. During culture of the stem cells, growth factors, such as stem cell factor, G-CSF, erythropoietin, thrombopoietin, IL-3, IL-6, IL-11, and IL-12, are often added to stimulate cell division and differentiation (see, e.g., PCT patent publication No. 94/18991 and EPO patent publication No. 611.263).

Such processes and therapies have been used not only for bone marrow transplantation but also for peripheral blood cell transplantation, replenishment of T cells in AIDS patients, replenishment of lymphocytes in Down's syndrome patients, replenishment of mature immune cells in aplastic anemia patients, and gene therapy. Gene therapy techniques in this context involve the introduction of a genetic construct into explanted cells, expansion of the clones that have incorporated the genetic construct, and then reintroduction of the altered cells into the host (see PCT patent publication Nos. 94/12629, 94/12633, 94/12649, and 94/12650). As methods for isolating cells and differentiating cells in culture continue to improve, the number of disease conditions that can be treated using such methods will increase. For instance, while bone marrow stem cells can be used to regenerate the various differentiated cells of the blood, embryonic and fetal stem cells can be used to regenerate the various differentiated cells of the entire body, offering many diverse applications of cell therapy.

The expansion of cells in culture involves many population doublings, however, so the cells obtained by cell therapy methods after expansion are much closer to senescence than the cells used to begin the process. By practicing the present invention in conjunction with the expansion step, one can prevent the cells from a net loss of telomeric DNA by lengthening telomeres during the expansion process, while the cells retain the primitive stem cell phenotype and express telomerase activity. The resulting cells are not any closer to senescence than the cells used to begin the process; in fact, the present method offers the possibility that the resulting cells may even have a greater replicative capacity than the cells used to begin the process.

For example, the method of the invention can be applied to bone marrow stem cells, some of which express at least a low level of telomerase activity but have finite replicative capacity. Telomerase activity can be detected in cell-free extracts of dividing, cultured hematopoietic stem and early progenitor cells but not other more differentiated dividing cells. As noted above, numerous kinds of ex vivo cell therapies using bone marrow stem cells are currently practiced or under development, and the present method can readily be practiced in conjunction with such methods. In cases where an individual is going to lose a large population of stem and hematopoietic cells, e.g., chemotherapy or radiation therapy, or is suffering from a disease linked to an immune system undergoing replicative senescence, e.g. normal aging, or cases where the immune system has been severely and chronically stressed, e.g., HIV infection, one can isolate bone marrow stem cells, culture or cultivate those cells in the presence of factors that increase telomere length to slow or reverse replicative senescence (as well as other factors, such as those noted above, if desired), and reintroduce the cells to strengthen or even to reconstitute the immune system.

In the case of AIDS, discussed above, the disease creates a condition in which $CD4^+$ cells are limiting, and death is caused by the early senescence of $CD4^+$ cells and the resulting unchecked infections by pathogens that follow. It is important to note that such cells age, because the replicative rate of the $CD4^+$ cells is increased as a result of HIV infection such that telomere attrition is caused at a greater rate than normal for such cells. The present invention provides therapeutic agents that can be used to treat such diseases and also provides diagnostic procedures by which immune senescence can be detected and appropriate therapeutic protocols followed.

The present invention provides a therapeutic protocol in which $CD4^+$ and/or CD8+ cells, or a population of cells containing or enriched for CD4+ and/or CD8+ cells, can be removed from the individual, preferably at an early stage when AIDS is first detected, stored in a bank, and then reintroduced after treatment with a telomere-lengthening reagent of the invention, into the individual at a later stage, i.e., when that individual no longer has a protective amount of $CD4^+$ and/or CD8+ cells available. Thus, an individual's life can be extended by a protocol involving continued administration of that individual's limiting cells at appropriate time points. These appropriate points can be determined by following $CD4^+$ and/or CD8+ cell senescence, or by determining the length of telomeres within such $CD4^+$ and/or CD8+ cells (as an indication of when those cells will become senescent). In the case of AIDS, currently practiced methods include those in which T cells, such as killer T cells, are isolated from a patient and expanded in culture (sometimes after gene therapy to introduce universal receptors for HIV) prior to reintroduction into the patient. The present invention can be used to lengthen the telomeres of such cells either directly or by treatment of a progenitor cells that is then cultured in vitro under differentiating conditions or allowed to differentiate in vivo.

Those of skill in the art will recognize that pluripotent hematopoietic stem cells differentiate when grown in culture and that various stimulatory agents, such as cytokines and antigens, can be used to influence the differentiation process. The present method can be practiced in conjunction with such methods to prepare high proliferative capacity cells of a particular type. In similar fashion, embryonic and fetal stem cells are totipotent or pluripotent and can be used to generate cells of any particular type (note that fibroblasts, liver cells, and keratinocytes can all be converted into muscle cells if transfected with vectors that express muscle differentiation factors such as myogenin and myoD). In addition, many late fetal tissues, such as muscle, lung, kidney, and adrenals, express telomerase activity and so are amenable to the telomere-lengthening methods of the invention. Consequently, the use of totipotent stem cells or telomerase-positive fetal cells in the present method offers significant benefits to the treatment of disease, particularly diseases associated with aging.

Thus, the present invention can be applied to generate cells with high proliferative capacity of a variety of tissue types, including: (a) cells of the central nervous system, including astrocytes, endothelial cells, and fibroblasts, which are involved in such age-related diseases as Alzheimer's disease, Parkinson's disease, Huntington's disease, and stroke; (b) cells of the integument, including fibroblasts, sebaceous gland cells, melanocytes, keratinocytes, Langerhan's cells, and hair follicle cells, which are involved in age-related diseases of the integument, such as dermal atrophy, elastolysis and skin wrinkling, sebaceous gland hyperplasia, senile lentigo, graying of hair and hair loss, chronic skin ulcers, and age-related impairment of wound healing; (c) cells of the articular cartilage, such as chondrocytes, the senescence of which leads to the overexpression of the destructive proteins collagenase and stromelysin, which destroy articular cartilage in osteoarthritis, and lacunal, synovial, connective tissue fibroblasts, which are involved in degenerative joint disease; (d) cells of the bone, such as osteoblasts, osteoclast progenitor cells, bone marrow stromal fibroblasts, and osteoprogenitor cells, which are involved in osteoporosis; (e) cells of the immune system such as B and T lymphocytes, monocytes, neutrophils, eosinophils, basophils, NK cells and their respective progenitors, which are involved in age-related immune system impairment; (f) cells of the vascular system, including endothelial cells, smooth muscle cells, and adventitial fibroblasts, which are involved in age-related diseases of the vascular system including atherosclerosis, calcification, thrombosis, and aneurysms; (g) cells of the eye, such as retinal pigmented epithelium, lens epithelial cells, iris muscle cells (myoblasts), and vascular endothelial cells, which are involved in loss of vision, i.e., age-related macular degeneration; (h) muscle satellite cells involved in muscular dystrophy; and (i) cells of the gut, such as intestinal epithelial cells, which are involved in malabsorption syndomes.

The present invention can therefore be applied to generate a variety of different cell types with high proliferative capacity. Regardless of cell type, practice of the method involves treating the cells with an olignucleotide substrate for telomerase. In general, such substrates can be identified by their ability to serve as primers for telomerase-mediated nucleotide addition to the 3'-end of the primer in an in vitro reaction. Although the oligonucleotide reagents of the invention can be identified by the property of ability to serve as a substrate for telomerase, the method of the invention in no way requires that the oligonucleotides actually be extended by telomerase in the cell for telomeres to be lengthened. The exact mechanism of action in vivo of the oligonucleotides is not known at this time and may involve titration of a repressor of telomerase or some other mechanism. Indeed, in one embodiment of the invention, no oligonucleotide substrate is required, and the method involves cultivating telomerase-positive cells under conditions where cell division is limited or completely inhibited for a period of time, typically several days to weeks and optionally months, sufficient for telomeres to be lengthened.

Preferably, however, the cells are treated in culture with an oligonucleotide substrate for telomerase in amounts sufficient to lengthen the telomeres of the cells. For human telomerase, such substrates include oligonucleotides that comprise a telomeric repeat sequence 5'-TTAGGG-3' (SEQ. ID. NO.2). In particular, oligonucleotides suitable for purposes of the present invention include the 9-, 12-, and 15-nucleotide versions of oligonucleotides that comprise the telomeric repeat sequence, i.e., 5'-TTAGGGTTA-3' (SEQ ID. NO.3) and 5'-TTAGGGTTAGGG-3' (SEQ. ID. NO.1). Other oligonucleotides that serve as telomerase substrates can also be employed, including the oligonucleotide 5'-TCGAGCACAGTT-3' (SEQ. ID. NO.4), which corresponds to the junction of a healed broken chromosome from a patient with thalassemia, and 5'-(GXGXGX)$_2$-3' (SEQ ID. NO.5), in which X can be independently selected at each position from either T or A, i.e., 5'-GTGAGTGAGTGA-3' (SEQ. ID. NO.5). Other oligonucleotide substrates for telomerase that can be used for purposes of the present invention have been described in the art or can readily be identified using assays described in the art; see, e.g., Morin, 3 October 1991, *Nature* 353:454–456.

Figure 1:
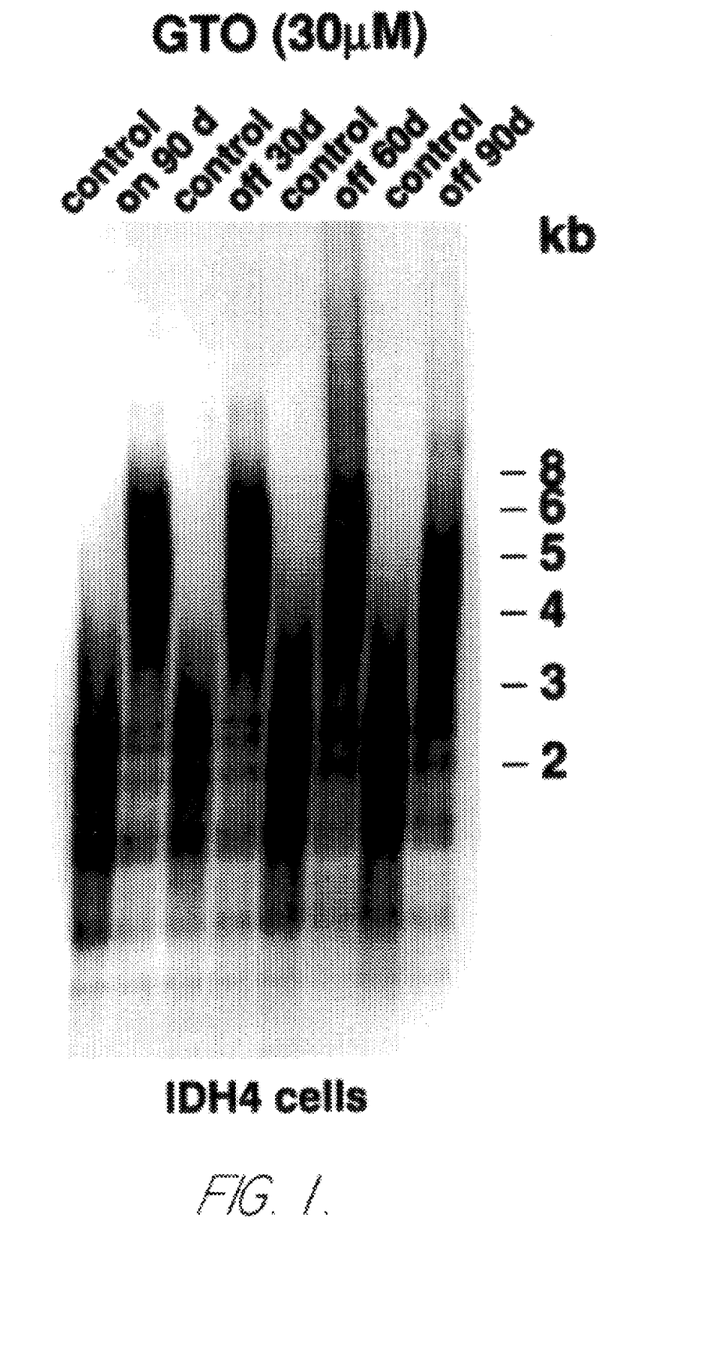
FIG. 1 shows the results of telomere length analysis (DNA was isolated from the cells, digested with a restriction enzyme that does not cleave telomeric repeat sequences, size-separated by gel electrophoresis, and probed with radioactively labeled probes comprising telomeric repeat sequences) of IDH4 cells treated according to the method of the invention as well as control cells. The telomeres of IDH4 cells elongate by several kbp after 90 days of thrice weekly treatment in culture with 30 μM GTR (for "G-rich Telomeric Repeat") oligonucleotide (5'-TTAGGGTTAGGG-3' (SEQ ID NO.1)). Lanes 1, 3, 5, and 7 show the results for control, untreated cells. Lane 2 shows the results for cells treated for 90 days with 30 μM GTR oligonucleotide. Lane 4 shows the results for cells treated for 90 days with 30 μM GTR oligonucleotide and then cultured for 30 days in the absence of added GTR oligonucleotide. Lane 6 shows the results for cells treated for 90 days with 30 μM GTR oligonucleotide and then cultured for 60 days in the absence of added GTR oligonucleotide. Lane 8 shows the results for cells treated for 90 days with 30 μM GTR oligonucleotide and then cultured for 90 days in the absence of added GTR oligonucleotide.
Figure 2:
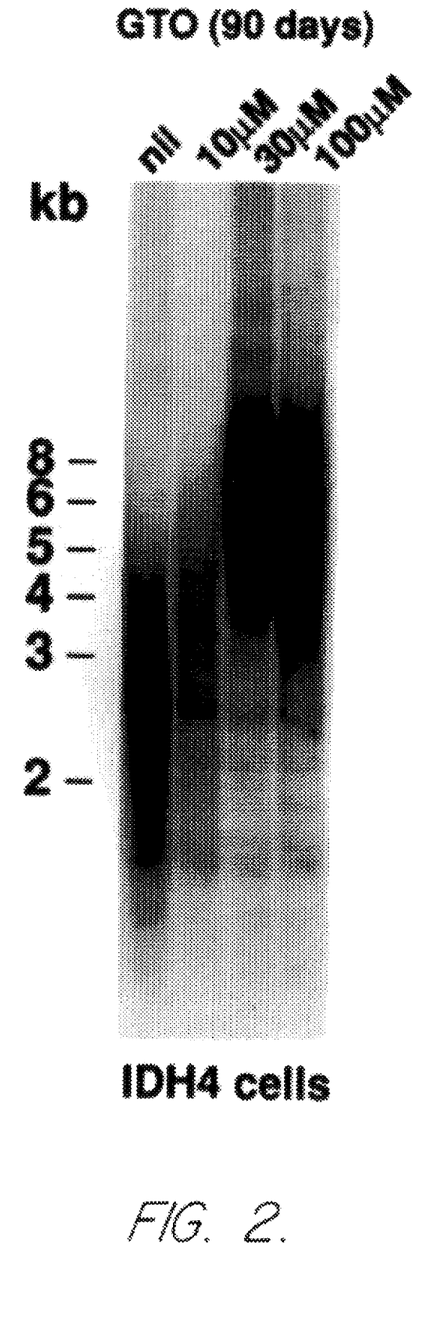
FIG. 2 shows the results of telomere length analysis of IDH4 cells treated according to the method of the invention as well as control cells and shows that a progressive (up to 30 μM) dose response is observed with increasing concentrations of the GTR oligonucleotide. Lane 1 shows the results for untreated control cells. Lane 2 shows the results for cells treated for 90 days with 10 μM GTR oligonucleotide. Lane 3 shows the results for cells treated for 90 days with 30 μM GTR oligonucleotide. Lane 4 shows the results for cells treated for 90 days with 100 μM GTR oligonucleotide.
Figure 3:
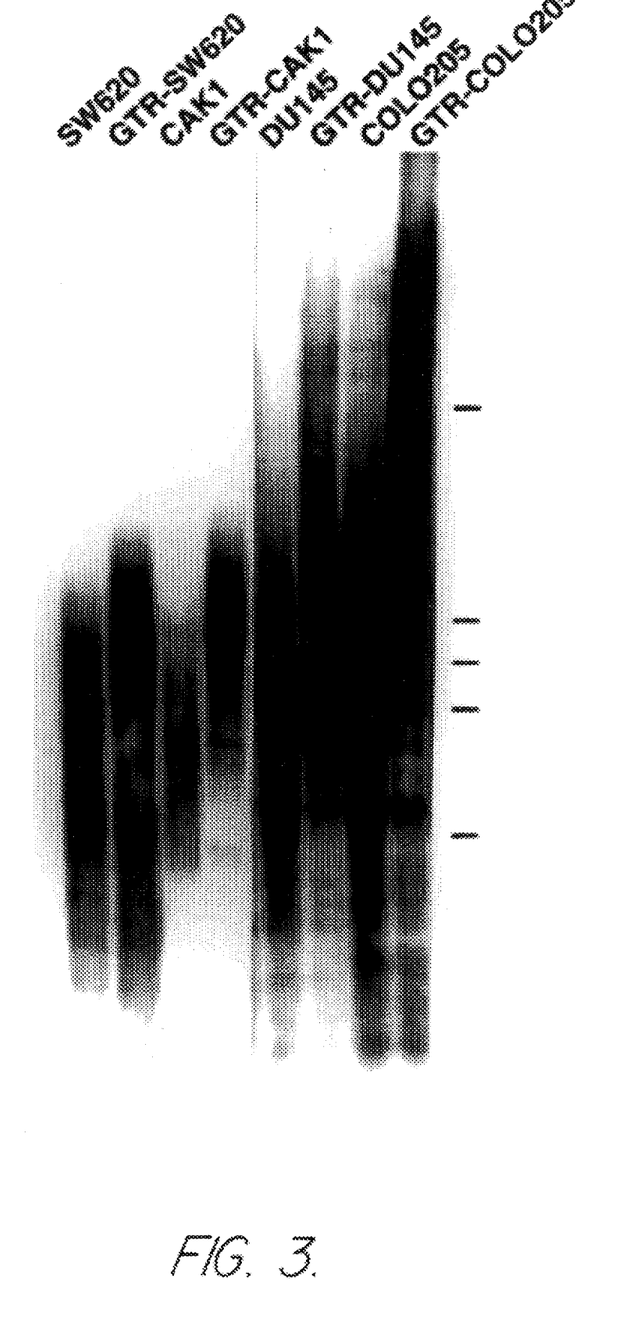
FIG. 3 shows the results of telomere length analysis of a variety of different cells treated according to the method of the invention as well as control cells and shows that the effect of the GTR oligonucleotide is not restricted to a few immortal cell lines, because all of the cell lines tested responded to GTR oligonucleotide treatment by elongating their telomeres. In addition to SW620 colon adenocarcinoma cells (lane 1, control, and lane 2, 30 μM GTR-treated cells after 20 population doublings), CAK1 renal carcinoma cells increase the length of their telomeres approximately the same amount as the SW620 GTR-treated cells (lane 3, control, and lane 4, GTR-treated cells) under the same condtions. In addition, DU145 prostatic adenocarcinoma cells and COLO205 colon carcinoma cells, which have slightly longer telomeres in control (untreated) cells, also elongate their telomeres in the presence of GTR oligonucleotide (lanes 5 and 7, controls, and lanes 6 and 8, GTR-treated, respectively) under the same conditions.

To illustrate how such oligonucleotides are used in the method of the present invention, IDH4, a line of T-antigen immortalized human lung fibroblasts, was cultured in the presence of increasing concentrations of an oligonucleotide containing two telomeric repeats, the GTR oligonucleotide described above. IDH4 cells express telomerase activity and have very short telomeres. FIG. 1 shows that the telomeres of IDH4 cells elongate by several kbp after 90 days (about 30 population doublings) of treatment in culture with the GTR oligonucleotide. This elongating effect can be seen both by the increasing size of the DNA resistant to digestion by restriction endonucleases (the "TRF" or "Terminal Restriction Fragment") and by the increasing signal following hybridization to oligonucleotides containing telomeric repeats. The effect is specific to the GTR oligonucleotide, because telomere elongation was not observed following treatment with either an oligonucleotide containing the complementary sequence (5'-CCCTAACCCTAA-3') (SEQ. ID. NO.7), called the "CTR" or "C-rich telomeric repeat" oligonucleotide, or a comparably sized oligonucleotide with a randomly selected sequence. The effect may be partially reversible, because IDH4 cells with elongated telomeres exhibited somewhat shorter telomeres when cultured in the absence of oligonucleotides (FIG. 1, lane 8, off 90 days). FIG. 2 shows that a progressive (up to 30 µM) dose response is observed with increasing concentrations of the GTR oligonucleotide. FIG. 3 shows that the effect of the GTR oligonucleotide is not restricted to a few immortal cell lines, because all of the cell lines tested responded to GTR oligonucleotide treatment by elongating their telomeres. SW620 human colon adenocarcinoma cells, which grow much faster than IDH4 cells, rapidly and progressively elongated their telomeres in the presence of 30 µM GTR oligonucleotide. The elongation was a continuous process that increased with increasing time of treatment. In addition to SW620 cells (lane 1, control, and lane 2, GTR-treated cells), CAK1 renal carcinoma cells increase the length of their telomeres approximately the same amount as the SW620 GTR-treated cells (FIG. 3, lane 3, control, and lane 4, GTR-treated cells). In addition, DU145 prostatic adenocarcinoma cells and COLO205 colon carcinoma cells, which have slightly longer telomeres in control (untreated) cells, also elongate their telomeres in the presence of GTR oligonucleotide (FIG. 3, lanes 4–8).

While these results were obtained with immortal cells lines to illustrate the invention, the telomere-lengthening effect of the oligonucleotides can be observed in normal cells that express telomerase activity. Methods for measuring telomerase activity have been described in the art (see, e.g., PCT patent publication No. 93/23572), and an especially preferred method is described in copending U.S. patent application Ser. No. 08/315,214, filed Sep. 28, 1994 (Harley et al.).

Other methods that can be useful in conjunction with the present invention include methods to measure telomere length, which may aid the practitioner in determining whether treatment according to the present method is needed for a particular cell type and whether such treatment has been effective. Procedures for measuring telomere length are known in the art. Typically, restriction endonuclease digestion is used (with enzymes which have a four-base recognition sequence, like HinfI, and do not cleave telomeric DNA) to cleave the genomic DNA; the cleaved fragments are separated according to molecular weight by agarose gel electrophoresis; and the gel is then dried and probed with a radioactively labelled probe, i.e., 5'-(TTAGGG)$_3$-3' (SEQ. ID. NO.7), complementary to telomeric DNA sequences.

As the results discussed above show, the oligonucleotides of the invention can be transferred into the cytoplasm of a cell spontaneously, i.e., without specific modification. One can also employ a variety of means to facilitate the uptake of an oligonucleotide by a cell. For instance, one can use liposomes that fuse with the cellular membrane or one can employ ligands that bind to surface membrane protein receptors of the cell resulting in endocytosis of the ligand together with any material bound to the ligand. Alternatively, the cells may be permeabilized to enhance transport of the oligonucleotides into the cell without injuring the cells. One can also use a DNA binding protein, e.g., HBGF-1, which is known to transport an oligonucleotide into a cell.

These delivery modes are useful both for cells in tissue culture (ex vivo) and in vivo. As already indicated, by using liposomes, particularly where the liposome surface carries ligands specific for target cells or are targetted to a specific organ, one can provide for the introduction of an oligonucleotide into the target cells in vivo. For instance, utilizing lipocortin's affinity for phosphatidyl serine, which is released from injured vascular endothelial cells, one can target an oligonucleotide to such a site. Alternatively, catheters, syringes, depots, or the like can be used to provide high localized concentrations of an oligonucleotide in vivo.

In related aspects, the invention features pharmaceutical compositions that include therapeutically effective amounts of the agents described above in pharmaceutically acceptable buffers. These pharmaceutical compositions can include one or more of these agents and be co-administered with other drugs. Compositions and products according to the invention may conveniently be provided in the form of solutions suitable for parenteral, nasal, or oral administration. In many cases, it will be convenient to provide an agent in a single solution for administration.

Amphoteric agents may be utilized as free bases, as acid addition salts, or as metal salts. The salts must, of course, be pharmaceutically acceptable, and these will include metal salts, particularly alkali and alkaline earth metal salts, e.g., potassium or sodium salts. A wide variety of pharmaceutically acceptable acid addition salts are available. These include those prepared from both organic and inorganic acids, preferably mineral acids. Typical acids that may be mentioned by way of example include citric, succinic, lactic, hydrochloric, and hydrobromic acids. Such products are readily prepared by procedures well known to those skilled in the art.

The agents of the invention can be provided as parenteral compositions for injection or infusion. The agents can, for example, be suspended in an inert oil, suitably a vegetable oil such as sesame, peanut, or olive oil. Alternatively, the agents can be suspended in an aqueous isotonic buffer solution at a pH of about 5.6 to 7.4. Useful buffers include sodium citrate-citric acid and sodium phosphate-phosphoric acid. The desired isotonicity can be achieved using sodium chloride or other pharmaceutically acceptable agents, such as dextrose, boric acid, sodium tartrate, propylene glycol, or other inorganic or organic solutes. Sodium chloride is preferred for buffers containing sodium ions.

If desired, solutions of the above compositions can be thickened with a thickening agent such as methyl cellulose. The solutions can be prepared in emulsified form, either water in oil or oil in water. Any of a wide variety of pharmaceutically acceptable emulsifying agents can be employed, including, for example, acacia powder or an alkali polyether alcohol sulfate or sulfonate.

The therapeutically useful compositions of the invention are prepared by mixing the ingredients following generally accepted procedures. For example, the selected components can be simply mixed in a blender or other standard device to produce a concentrated mixture that can then be adjusted to the final concentration and viscosity by the addition of water or thickening agent and possibly a buffer to control pH or an additional solute to control tonicity.

For use by the physician, the compositions can be provided in dosage unit form containing an amount of agent that will be effective in one or multiple doses to perform the desired function. As will be recognized by those in the field, an effective amount of therapeutic agent will vary with many factors, including the age and weight of the patient, the patient's physical condition, and other factors.

Selected agents, e.g., oligonucleotides and pharmaceutical compositions of the same, can be administered prophylactically or to patients suffering from disease, e.g., by exogenous delivery of the agent to an infected tissue by means of an appropriate delivery vehicle, e.g., a liposome, a controlled release vehicle, by use of iontophoresis, electropotation, or ion-paired molecules, or covalently attached adducts, and other pharmacologically approved methods of delivery. Routes of administration include intramuscular, aerosol, oral (tablet or pill form), topical, systemic, ocular, intraperitoneal, and/or intrathecal. Gene therapy administered using recombinant expression vectors encoding a therapeutic oligonucleotide of the invention can also be used to deliver an oligonucleotide to a cell.

The specific delivery route of any selected agent will depend on the use of the agent. Generally, a specific delivery program for each agent will focus on naked agent uptake with regard to intracellular localization, followed by demonstration of efficacy. Alternatively, delivery to the same cells in an organ or tissue of an animal can be accomplished. Uptake studies can include uptake assays to evaluate cellular oligonucleotide uptake, regardless of the delivery vehicle or strategy. Such assays will also determine the intracellular localization of the agent following uptake, ultimately establishing the requirements for maintenance of steady-state concentrations within the cellular compartment containing the target sequence (nucleus and/or cytoplasm). Efficacy and cytotoxicity can also be tested. Toxicity studies will address not only cell viability but also cell function.

Some methods of delivery suitable for oligonucleotides include: encapsulation in liposomes; transduction by retroviral vectors; and conjugation with agents that direct delivery to certain sites withing the body. At least three types of delivery strategies are useful in the present invention, including: agent modification, particle carrier delivery vehicles, and retroviral expression vectors. Unmodified agents may be taken up by cells slowly and inefficiently. To enhance cellular uptake, an agent can be modified to reduce charge but maintain specific functional groups to improve diffusion across the cell membrane.

Modification of agents to reduce charge is one approach to enhance the cellular uptake of these larger molecules. The structural requirements necessary to maintain agent activity are well understood by those in the art. These requirements are taken into consideration when designing modifications to enhance cellular delivery. The modifications are also designed to reduce susceptibility to enzymatic degradation. Both of these characteristics should greatly improve the efficacy of the agent. Chemical modifications of the phosphate backbone of oligonucleotides will reduce the negative charge, allowing free diffusion of the oligonucleotide across the membrane.

In the body, maintenance of an external concentration is necessary to drive the diffusion of the modified oligonucleotides into the cells of the tissue. Administration routes that allow the diseased tissue to be exposed to a transient high concentration of the oligonucleotide, which is slowly dissipated by systemic adsorption, can be used. Intravenous administration with a drug carrier designed to increase the circulation half-life of the oligonucleotides can also be used. The size and composition of the drug carrier restricts rapid clearance from the blood stream. The carrier, made to accumulate at the site of infection, can protect the oligonucleotides from degradative processes.

Drug delivery vehicles are effective for both systemic and topical administration. The vehicles can be designed to serve as a slow release reservoir or to deliver their contents directly to the target cell. An advantage of using direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles that fall into this category are liposomes, hydrogels, cyclodextrins, biodegradable nanocapsules, and bioadhesive microspheres. For instance, nanoparticles and hydrogels have been used as delivery vehicles for chemotherapeutic agents and protein-based pharmaceuticals.

Liposomes increase extracellular stability, increase uptake efficiency and improve biological activity. Liposomes are hollow spherical vesicles composed of lipids arranged in a similar fashion as those lipids that make up the cell membrane. Liposomes have an internal aqueous space for entrapping water soluble compounds and range in size from 0.05 µm to several microns in diameter. Several studies have shown that liposomes can deliver agents to cells in biologically active form. For example, a liposome delivery vehicle originally designed as a research tool, lipofectin, has been shown to deliver intact mRNA molecules to cells yielding production of the corresponding protein. Liposomes offer several advantages: liposomes are non-toxic and biodegradable in composition; liposomes display long circulation half-lives; and recognition molecules can be readily attached to liposome surfaces for targetting to tissues. Finally, cost effective manufacture of liposome-based pharmaceuticals, either in a liquid suspension or lyophilized product, has demonstrated the viability of this technology as an acceptable drug delivery system.

Topical administration of agents is advantageous, because topical administration allows localized concentration at the site of administration with minimal systemic adsorption. This simplifies the delivery strategy of the agent to the disease site and reduces the extent of toxicological characterization. Furthermore, the amount of material to be applied is far less than that required for other administration routes. Effective delivery requires the agent to diffuse into the target cells. Chemical modification of the agent to neutralize negative or positive charges can in some instances enhance penetration. The modified agent can also be co-formulated with permeability enhancers, such as azone or oleic acid, in a liposome. The liposomes can either represent a slow release presentation vehicle in which the modified agent and permeability enhancer transfer from the liposome into the targeted cell, or the liposome phospholipids can participate directly with the modified agent and permeability enhancer in facilitating cellular delivery. In some cases, both the agent and permeability enhancer can be formulated into a suppository formulation for slow release.

Agents can also be systemically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal, and ophthalmic. Each of these administration routes exposes the agent to an accessible diseased or other tissue. Subcutaneous administration drains into a localized lymph node and proceeds through the lymphatic network into the circulation. The rate of entry into the circulation has been shown to be a function of molecular weight and size. The use of a liposome or other drug carrier localizes the agent at the lymph node. The agent can be modified to diffuse into the cell, or the liposome can directly participate in the delivery of either the unmodified or modified agent to the cell.

Thus, delivery methods include liposomes, hydrogels, controlled-release polymers, microinjection, electroporation (for ex vivo treatments), and other pharmaceutically applicable methods. The dosage will depend upon the disease indication and the route of administration but can be between 10–2000 mg/kg of body weight/day. The duration of treatment will extend through the course of the disease symptoms, usually at least 14–16 days and in some indications continuously. Multiple daily doses are anticipated for topical applications, ocular applications, and vaginal applications. The number of doses will depend upon delivery vehicle and efficacy data from clinical trials.

Establishment of therapeutic levels of agent within the target cell is dependent upon the rate of uptake and degradation. Decreasing the degree of degradation will prolong the intracellular half-life of the agent. Thus, chemically modified agents, e.g., oligonucleotides with modification of the phosphate backbone, or capping of the 5' and 3' ends of the oligonucleotides with nucleotide analogues, can be used but may require different dosaging.

While the invention is described in a manner that focuses on therapeutic methods for humans and human cells, the method may be applied to cells of any source, particularly cell of animals such as primates and domestic animals such as equine, bovine, arian, ovine, porcine, feline, and canine animals. Other features and advantages of the invention will be apparent from the following description of the preferred embodiments thereof, and from the claims. The following examples are offered by way of illustration and not by way of limitation.

EXAMPLES

The following examples illustrate specific aspects of the invention. The examples are not limiting but rather are intended to provide an indication of specific methodology useful in practice of the invention as well as demonstrating the utility of the invention to increase telomere length and slow the onset of cellular senescence. Such correlation indicates to those in the art the breadth of the invention beyond these examples.

EXAMPLE 1

Increasing Telomere Length with GTR Oligonucleotide

An immortalized human fibroblast cell line, IDH4, which has very short TRFs, was incubated with GTR oligonucleotide. Referring to FIGS. 1–3, cells were incubated in regular culture medium containing serum in the presence of 10 μM, 30 μM, and 100 μM GTR oligonucleotide. The cells were fed fresh phosphodiester GTR oligonucleotide thrice weekly and subcultured when confluent for a total of 90 days. The cells were still growing in GTR oligonucleotide after 90 days at all concentrations used. When TRF analysis was performed after 90 days, the IDH4 cells were shown have increased TRF length in a dose dependent manner with 30 μM and 100 μM having approximately the same effect. The control and 30 μM GTR oligonucleotide-treated cells were passaged without oligonucleotide addition for an additional 90 days (approximately 35–40 PDL). As is illustrated in FIG. 1, the TRFs slowly shorten.

FIG. 1 shows that the telomeres of IDH4 cells elongate by several kbp after 90 days (about 30 population doublings) of treatment in culture with the GTR oligonucleotide. This elongating effect can be seen both by the increasing size of the DNA resistant to digestion by restriction endonucleases and by the increasing signal following hybridization to oligonucleotides containing telomeric repeats. The effect is specific to the GTR oligonucleotide, because telomere elongation was not observed following treatment with either an oligonucleotide containing the complementary sequence, or a comparably sized oligonucleotide with a randomly selected sequence. The effect may be partially reversible, because IDH4 cells with elongated telomeres exhibited somewhat shorter telomeres when cultured in the absence of oligonucleotides (FIG. 1, lane 8, off 90 days).

FIG. 2 shows that a progressive (up to 30 μM) dose response is observed with increasing concentrations of the GTR oligonucleotide. FIG. 3 shows that the effect of the GTR oligonucleotide is not restricted to a few immortal cell lines, because all of the cell lines tested responded to GTR oligonucleotide treatment by elongating their telomeres. SW620 human colon adenocarcinoma cells, which grow much faster than IDH4 cells rapidly and progressively elongated their telomeres in the presence of 30 µM GTR oligonucleotide. The elongation was a continuous process that increased with increasing time of treatment. In addition to SW620 cells (lane 1, control, and lane 2, GTR-treated cells), CAK1 renal carcinoma cells increase the length of their telomeres approximately the same amount as the SW620 GTR-treated cells (FIG. 3, lane 3, control, and lane 4, GTR-treated cells). In addition, DU145 prostatic adenocarcinoma cells and COLO205 colon carcinoma cells, which have slightly longer telomeres in control (untreated) cells, also elongate their telomeres in the presence of GTR oligonucleotide (FIG. 3, lanes 4–8).

EXAMPLE 2

Increasing Lifespan of Cells

The ability to manipulate telomere length makes possible the demonstration that telomere length determines the lifespan of cells. Cell hybrids were constructed between normal diploid BJ foreskin fibroblasts and either (1) immortal IDH4 cells; or (2) immortal IDH4 cells with telomeres elongated by the method of the present invention. Young BJ cells with approximately 60 doublings left in their normal in vitro lifespan were used to ensure that the normal telomeres would not be limiting for the hybrid lifespan.

Fifty clones from each combination were picked and followed to determine their proliferative capacity. The loss of a few normal chromosomes from these hybrids can potentially result in the generation of immortal segregants. To recduce the possibility that a rare segregant would overgrow the population and mask the cessation of growth by the bulk of the cells, the hybrid clones were maintained at low population sizes by serial clonal subcultivation. At each passage, the dishes were scanned, and an average sized clone was picked and replated. Cell counts of parallel dishes of the population of hybrids plated at clonal density indicated that each passage corresponded to approximately 13–14 cell divisions.

More than 95% of the hybrid clones between the immortal IDH4 cells without elongated telomeres and normal BJ fibroblasts ceased proliferating before the third serial subcloning, indicating that such hybrids were only able to undergo approximately 26–39 doublings. In contrast, most of the hybrid clones between the IDH4 cells with elongated telomeres and BJ fibroblasts were able to be maintained for two or more additional passages. The proliferative capacity of the hybrids was thus extended at least an additional 26 doublings by using IDH4 cells whose telomeres were approximately 2 kb longer than the parental IDH4 cells.

To ensure that the above results were not biased by the choice of which subclone was selected for subcultivation, the comparison of the lifespan of the two hybrids was repeated using a protocol desinged to determine the lifespan of populations of clones. Hybrids were plated at clonal density in duplicate. After clones had formed, one dish was fixed and counted to determine the number of clones per dish, and one dish was trypsinized and counted to determine the number of cells per dish and then replated to form the next generation of subclones. This permitted the number of cells per clone and thus the average nubmer of cell divisions per passage to be determined. Because dishes containing 100–300 clones were used, the results represent the average of a large number of clones. An additional set of hybrids, comparing parental SW620 cells and SW620 that had been treated with $(TTAGG)_2$ (SEQ. ID. NO.8) to elongate its telomeres, was also constucted to verify that the extension of hybrid lifespan was not specific to IDH4 cells. The results showed that the proliferative lifespans of the hybrid cells with elongated telomeres was increased relative to the hybrids with shorter telomeres.

Methods similar to those described in this example can be used to create human hybridoma cell lines with increased proliferative capacity. In this aspect of the invention, an immortal human cell, such as a myeloma cell, is treated according to the method of the present invention to increase telomere length and then fused to a human antibody-producing cell. The resulting cell hybrids have increased proliferative capacity as compared to human hybridoma cells made by methods currently available in the art.

As shown by the above results, by modulating telomere length, one may increase the proliferative capacity of cells and therefore treat disease and disease conditions associated with cellular senescence. All publications and patent applications cited in this specification are herein incorporated by reference as if each individual publication or patent application was specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method for increasing the proliferative capacity of normal cells having telomerase activity, which method comprises culturing or cultivating said cells in the presence of an oligonucleotide substrate for telomerase under conditions such that said oligonucleotide substrate enters said cells and acts to lengthen telomeric DNA of said cells and the proliferative capacity of said cells is increased.

2. The method of claim 1, wherein said oligonucleotide substrate for telomerase consists of an oligonucleotide sequence selected from the group consisting of 5'-TTAGGG-3' (SEQ ID NO 2), 5'-TTAGGGTTA-3'(SEQ ID NO 3), 5'-TTAGGGTTAGGG-3'(SEQ ID NO 1), 5'-TCGAGCACAGTT-3'(SEQ ID NO 4), and 5'-(GXGXGX)$_2$-3' (SEQ ID NO 5), in which X can be independently selected at each position from either T or A.

3. A method of making human hybridoma cells with increased proliferative capacity, said method comprising:

(a) culturing an immortal cell line in the presence of an oligonucleotide substrate for telomerase under conditions such that the telomeres in cells of said cell line lengthen, anti the proliferative capacity of said cells is increased; and (b) fusing said cells cultured in step (a) with human antibody-producing cells to produce said hybridoma cells.

* * * * *